United States Patent
Casar et al.

(10) Patent No.: US 8,207,333 B2
(45) Date of Patent: Jun. 26, 2012

(54) PROCESS FOR PREPARING PURE AMORPHOUS ROSUVASTATIN CALCUIM

(75) Inventors: Zdenko Casar, Logatec (SI); Marko Zlicar, Celje (SI)

(73) Assignee: Lek Pharmaceuticals d. d., Ljubljana (SI)

( * ) Notice: Subject to any disclaimer, the term of this patent is extended or adjusted under 35 U.S.C. 154(b) by 1057 days.

(21) Appl. No.: 11/916,599

(22) PCT Filed: Jun. 22, 2006

(86) PCT No.: PCT/EP2006/006008
§ 371 (c)(1),
(2), (4) Date: Jan. 7, 2008

(87) PCT Pub. No.: WO2006/136408
PCT Pub. Date: Dec. 28, 2006

(65) Prior Publication Data
US 2008/0188504 A1    Aug. 7, 2008

(30) Foreign Application Priority Data

Jun. 24, 2005  (SI) .................... P200500187

(51) Int. Cl.
*C07D 239/02* (2006.01)
(52) U.S. Cl. ........................................ 544/242
(58) Field of Classification Search .......... 544/242; 514/256
See application file for complete search history.

(56) References Cited

U.S. PATENT DOCUMENTS

| 5,260,440 | A | 11/1993 | Hirai et al. |
| 6,844,437 | B1 | 1/2005 | Koike et al. |

FOREIGN PATENT DOCUMENTS

| WO | WO 00/49014 | * | 8/2000 |
| WO | 0160804 | | 8/2001 |
| WO | 2005023778 | | 3/2005 |
| WO | WO 2005/023778 | * | 3/2005 |
| WO | 2005040134 | | 5/2005 |
| WO | 2005077917 | | 8/2005 |
| WO | 2006035277 | | 4/2006 |

* cited by examiner

*Primary Examiner* — Paul V. Ward
(74) *Attorney, Agent, or Firm* — Luedeka Neely Group, P.C.

(57) ABSTRACT

A new process for preparing pure amorphous rosuvastatin calcium, substantially free of impurities, is disclosed. A process comprising hydrolysing a $C_1$ to $C_5$ alkyl ester of rosuvastatin, preferably methyl rosuvastatin or tert-butyl rosuvastatin, with a base, e.g. sodium hydroxide, in the presence of an aprotic solvent, preferably tetrahydrofuran and N,N-dimethyl acetamide, or in the presence of a mixture of an aprotic solvent and water, to obtain a solution of rosuvastatin salt, which may be converted to another rosuvastatin salt using another cation, e.g. with calcium cation to obtain rosuvastatin calcium. Rosuvastatin amine salts may be obtained as well. In another preferred aspect of the invention rosuvastatin free acid may be converted to various rosuvastatin salts, e.g. to rosuvastatin calcium, rosuvastatin sodium or various rosuvastatin amine salts, including rosuvastatin solvates, e.g. rosuvastatin calcium hydrate.

Rosuvastatin calcium is useful in the treatment of hyperlipidemia, hypercholesterolemia and atherosclerosis.

38 Claims, 3 Drawing Sheets

PROCESS FOR PREPARING PURE AMORPHOUS ROSUVASTATIN CALCUIM

This application is the National Stage of International Application No. PCT/EP2006/006008, filed on Jun. 22, 2006, which claims benefit under 35 U.S.C §119 of Slovenian Patent application P200500187 filed on Jun. 24, 2005, the contents of both are incorporated herein by reference in their entirety.

FIELD OF THE INVENTION

The present invention relates to a new process for preparing pure amorphous rosuvastatin calcium, substantially free of impurities.

BACKGROUND OF THE INVENTION

Rosuvastatin is generic name for (+)-7-[4-(4-fluorophenyl)-6-isopropyl-2-(N-methyl-N-methylsulfonylamino)pyrimidin-5-yl]-(3R,5S)-dihydroxy-(E)-heptenoic acid administered in the therapy as its calcium salt as commercial drug, and illustrated in Formula 1 hereinafter, which compound is an inhibitor of the enzyme 3-hydroxy-3-methylglutaryl-co-enzyme A reductase (HMG CoA reductase), useful in the treatment of hyperlipidemia, hypercholesterolemia and atherosclerosis. Rosuvastatin and the synthesis of rosuvastatin calcium was first disclosed in patent EP-B-521 471; in the last two steps of the whole synthesis provided by hydrolysis of methyl ester of rosuvastatin (methyl rosuvastatin) in polar solvent, e.g. ethanol, in the presence of a base, following by isolation of sodium salt of rosuvastatin (sodium rosuvastatinate) and converting said sodium salt of rosuvastatin with a water soluble calcium salt under aqueous conditions to calcium salt of rosuvastatin. The process for the preparation of the intermediates disclosed in EP-B-521 471 patent is incorporated herein by reference.

WO 2005/023778 discloses a process for the preparation of rosuvastatin calcium by conversion of $C_1$ to $C_4$ alkyl ester of rosuvastatin, preferably tert-butyl ester of rosuvastatin with a base, preferably sodium hydroxide, in the presence of a $C_1$ to $C_4$ alcohol, preferably ethanol, to a solution of rosuvastatin salt, e.g. its sodium salt and converted said salt into rosuvastatin calcium by adding a source of calcium to said solution.

A novel crystalline form of rosuvastatin calcium can be prepared by crystallization of amorphous form of rosuvastatin calcium from a mixture of: (i) water and acetonitrile in the ratio of 1:1 by volume; (ii) water and acetone in the ratio of 1:1 by volume; or water, methanol and tert-butyl methyl ether in the ratio of 1:1:1 by volume, what is described in WO 2000/042024.

WO 2005/040134 describes amorphous rosuvastatin calcium having a purity of more than 99% obtained from known crystalline rosuvastatin calcium. Said crystalline form may be prepared by crystallization of amorphous rosuvastatin calcium which process is known from the prior art.

Formula 1

Figure 1:
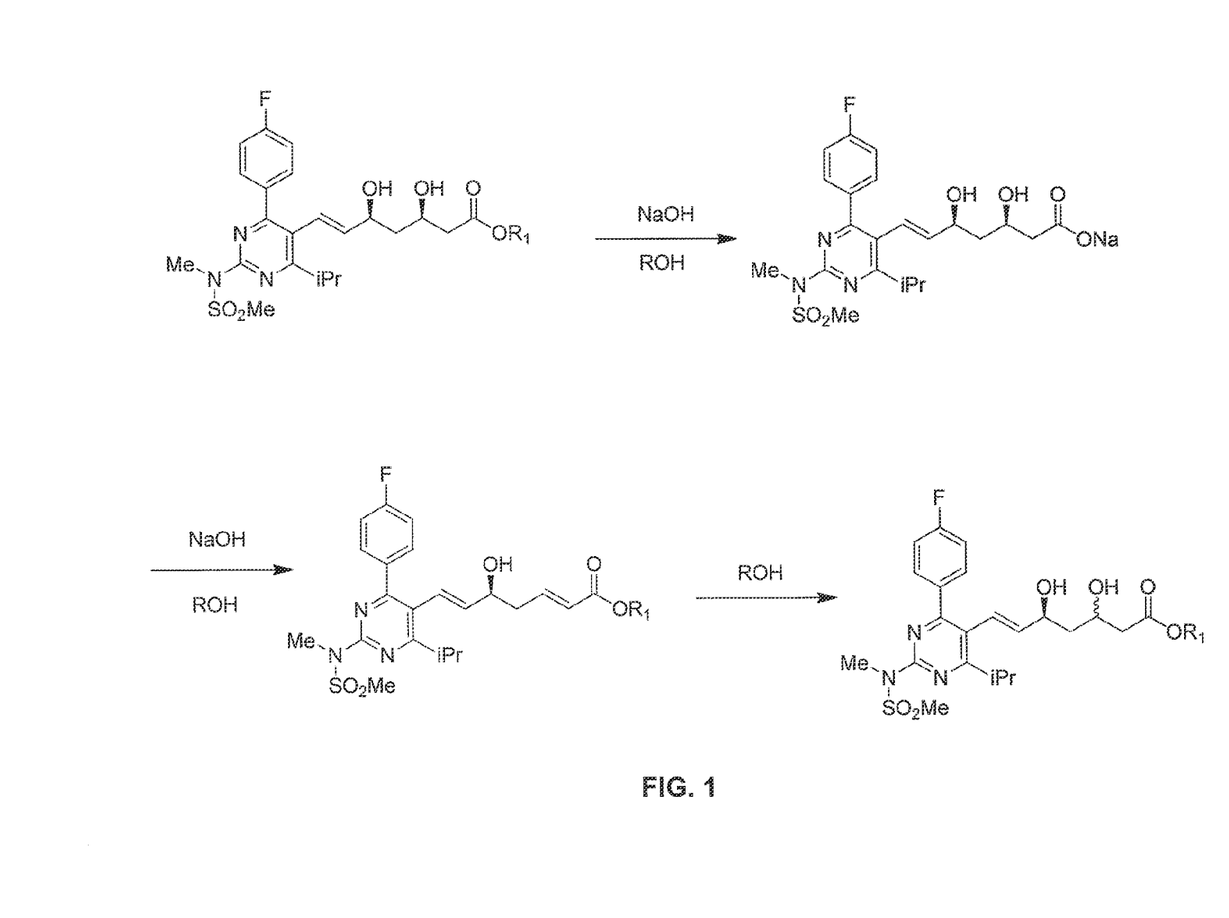
FIG. 1 is an illustration of a prior art reaction scheme for the production of rosuvastatin sodium.

It is well known that alkali metal salts of organic carboxylic acids are often hygroscopic what may cause problems at isolation. Indeed the isolation of sodium salt of rosuvastatin, which can be an intermediate in preparing rosuvastatin calcium salt, might be unrepeatable in yield and physical state what depends on the reaction conditions and evaporation of solvents, which is difficult to control. International publication WO 05/23778 tried to avoid said problems without isolating rosuvastatin sodium salt by extraction of impurities from its aqueous solution, but by using $C_1$ to $C_4$ alcohols as reaction medium a risk of conversion into specific impurities still existed. Namely, it is known that β-hydroxy acids in alcoholic alkali solution are submitted to dehydration what may lead after realkoxylation into special side products (see the reaction Scheme of FIG. 1, wherein R and $R_1$ independently denotes $C_1$ to $C_5$ alkyl group), O-alkyl rosuvastatin, e.g. O-ethyl rosuvastatin.

Figure 2:
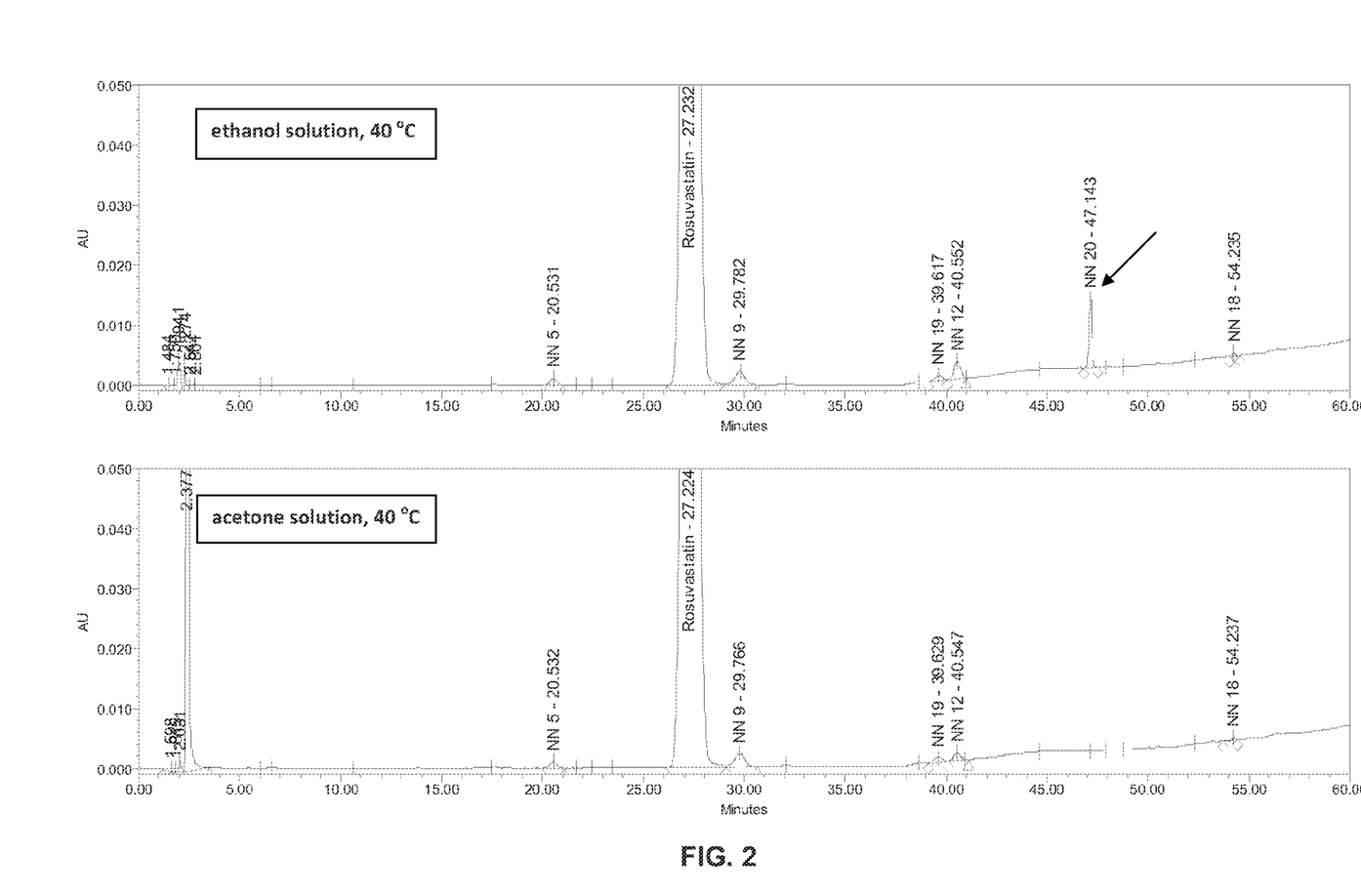
FIG. 2 is a set of graphs illustrating the stability of rosuvastatin in an alcohol solution as compared to an acetone solution.

From the results of stress stability test photographed on FIG. 2 it is obvious that rosuvastatin was submitted to specific degradation in ethanol as alcoholic medium. The specific impurity, designated as NN 2047.143 is O-ethyl ether derivative (see the reaction Scheme of FIG. 1 wherein R denotes ethyl (Et) group), was detected in 0.35% area by HPLC in comparison with acetone solution in which no such impurity was observed.

Therefore a need for an efficient process for preparing pure rosuvastatin calcium, without any significant amounts of side products, still exists.

SUMMARY OF THE INVENTION

In a first aspect the present invention provides a process for producing calcium salt of rosuvastatin comprising:
  a) hydrolysing a $C_1$ to $C_5$ alkyl ester of rosuvastatin with a base in the presence of an aprotic solvent or with a base in the presence of a mixture of aprotic solvent and water, to obtain a solution of rosuvastatin salt,
  b) converting thus obtained rosuvastatin salt with a source of calcium to obtain rosuvastatin calcium
  c) isolating the calcium salt of rosuvastatin.

In another aspect of the invention the $C_1$ to $C_5$ ester of rosuvastatin may be converted to solid sodium salt of rosuvastatine, which is isolated from the obtained solution; said isolated salt having excellent handling physical properties.

In a further aspect of the invention the rosuvastatin free acid ("rosuvastatinic acid") may be isolated according to the procedure comprising:
  a) hydrolysing a $C_1$ to $C_5$ alkyl ester of rosuvastatin with a base in an aprotic solvent, optionally diluted with water,
  b) removing excess of organic aprotic solvent,
  c) optionally diluting water poor solution with additional water, d) optionally washing thus obtained aqueous solution of rosuvatatin salt of a base with a water immiscible organic solvent, e) acidifying aqueous solution of rosuvastatin salt of a base, f) extracting the resulted rosuvastatin acid with the water immiscible organic solvent, g) removing the water immiscible organic solvent from the obtained extract to obtain isolated rosuvastatin acid.

Yet another aspect of the invention presents a conversion of thus obtained rosuvastatin acid (rosuvastatinic acid) to any salt of rosuvastatin, e.g. to its sodium or calcium salt, by simple adding cation source in a solvent to rosuvastatin acid.

By conversion of rosuvastatin acid into its calcium salt in nonaqueous medium substantially anhydrous rosuvastatin calcium salt may be obtained.

Yet another aspect of the invention presents a new more convenient procedure of preparing of monohydrates of rosuvastatin calcium.

Rosuvastatin calcium prepared by such improved procedures according to the invention has at least 99.5% of chromatographic purity; moreover when using very pure starting $C_1$ to $C_5$ rosuvastatin ester of the invention more than 99.8% purity, even more, in some cases more than 99.9% of chromatographic purity of desired rosuvastatin calcium may be obtained.

The term "chromatographic purity" means purity as determined by HPLC ("High Pressure Liquid Chromatography").

And in final aspect of the invention provides for a pharmaceutical formulation comprising rosuvastatin calcium prepared according to above described process and a method of treatment of hyperlipidemia, hypercholesterolemia and atherosclerosis, comprising the step of administering the said pharmaceutical formulation to the mammal in need thereof.

The starting ester may be preferably methyl ester of rosuvastatin, more preferably tert-butyl ester of rosuvastatin (tert-butyl rosuvastatin).

Any aprotic solvent of step a) of above described process may be used in the reaction, preferably tetrahydrofuran (THF) or N,N-dimethylacetamide (DMA).

The base used in the above described process of step a) is selected from the group consisting of sodium hydroxide, potassium hydroxide, and their analogues.

Any appropriate source of calcium source may be used, preferably calcium chloride or calcium acetate.

The water immiscible solvent used in above steps d) and f) is selected from the group consisting of $C_1$-$C_4$ esters, e.g. acetate esters, preferably ethyl acetate (AcOEt), ethers, chlorinated hydrocarbons, cyclic hydrocarbons.

As acid for acidifying aqueous solution in step e) of above described process any inorganic acid or organic acid may be used, such as hydrochloric acid or sulfuric acid.

The term "rosuvastatin acid" means (+)-7-[4-(4-fluorophenyl)-6-isopropyl-2-(N-methyl-N-methylsulfonylamino)pyrimidin-5-yl]-(3R,5S)-dihydroxy-(E)-6-heptenoic acid.

BRIEF DESCRIPTION OF THE DRAWINGS

The above and other aspects and advantages of the invention will now be further described in conjunction with the accompanying drawings in which.

DETAILED DESCRIPTION OF THE INVENTION

An object of the present invention is to find a novel process for the preparation of pure amorphous rosuvastatin calcium, substantially free of impurities, which would avoid the use of alcohols, e.g. $C_1$ to $C_4$ alcohol as a reaction medium known in the prior art processes, thus resulting to elimination O-alkyl rosuvastatin impurities (see the reaction Scheme of FIG. 1), e.g. O-ethyl rosuvastatin, containing in rosuvastatin calcium, prepared according to the prior art processes.

Further is the object of the present invention to find a novel process which would enable easy and simple preparation and isolation of intermediary rosuvastatin salt, e.g. rosuvastatin sodium or rosuvastatin acid, in good quality, crystallinity and repeatedly, which were difficult to isolate in the prior art processes and which would enable simple and easy conversion of said intermediary compounds to desired commercial rosuvastatin calcium.

The term "substantially free of impurities" means less than 0.5% of total impurities as measured by area percentage HPLC, preferably less than 0.2% of total impurities as measured by area percentage HPLC, most preferably less than 0.1% of total impurities as measured by area percentage HPLC.

We have unexpectedly and surprisingly found that above problem has been solved by hydrolysis of starting $C_1$ to $C_5$ alkyl esters of rosuvastatin, where instead of using $C_1$ to $C_4$ alcohols as solvent medium known in the prior art processes said hydrolysis take place in an aprotic solvents with added water. Any suitable aprotic solvent may be used, but preferably tetrahydrofuran (THF) and N,N-dimethylacetamide (DMA).

In the first aspect of the invention a $C_1$ to $C_5$ alkyl ester of rosuvastatin, where alkyl denotes methyl, ethyl, n-propyl, iso-propyl, n-butyl, iso-butyl, tert-butyl, amyl and tert-amyl group, most preferably tert-butyl ester of rosuvastatin, is reacted with a base in an aprotic solvent—water mixture, preferably with sodium hydroxide as a base, in tetrahydrofuran (THF) containing medium, which may be in the mixture with other solvents, preferably THF and water mixture in all ratios, more preferably the mixture of tetrahydrofuran and water in the ratio of 5:1 to 1:5 by volume. Pure THF may be employed as medium as well. After completing of said hydrolysis reaction preferably rosuvastatin sodium is obtained. Hydrolysis of starting $C_1$ to $C_5$ ester of rosuvastatin may be performed at temperatures from 20° C. to 60° C. The hydrolysis is accomplished in 30 minutes (at 60° C.) to 2 hours (at 20° C.). Thereafter the obtained reaction mixture may be diluted with another solvent, preferably with water, if aqueous poor hydrolysis medium has been previously used. The aprotic organic solvent is then optionally removed, the residual aqueous solution is washed by water immiscible organic solvent selected from the group consisting of esters, ethers, chlorinated hydrocarbons or cyclic hydrocarbons, preferably more user friendly solvents, e.g. acetate esters, more preferably ethyl acetate (AcOEt), or cyclic hydrocarbons, to obtain aqueous solution of pure rosuvastatin alkaline salt, preferably sodium salt of rosuvastatin.

Alternatively, after said hydrolysis in water rich media, the reaction mixture is washed by water immiscible organic solvents selected from the group consisting of esters, ethers, chlorinated hydrocarbons or cyclic hydrocarbons, preferably selected from more user friendly solvents, e.g. acetate esters or cyclic hydrocarbons, more preferably ethyl acetate, without previous partial evaporation of organic component of the mixture with water, for example tetrahydrofuran.

Thereafter a source of calcium ions is added to the solution of rosuvastatin salt, preferably to the solution of rosuvastatin sodium salt, for instance calcium halogenide, preferably calcium chloride, and another calcium source, for example calcium nitrate or calcium hydroxide, calcium salt of $C_1$-$C_{20}$ alkanoic acid, preferably calcium palmitate, calcium pivalate or calcium acetate. The most preferable calcium source is calcium acetate monohydrate ($Ca(OAc)_2 \times H_2O$). Addition of $Ca(OAc)_2 \cdot H_2O$ may be performed at temperatures between 0° C. to 40° C. $Ca(OAc)_2 \times H_2O$ may be added in one portion or dropwise in 5 to 60 minutes. After the addition of $Ca(OAc)_2 \times H_2O$ resulted suspension may be stirred at temperatures from 0° C. to 40° C. from 30 minutes to 2 hours. The desired rosuvastatin calcium may be formed as a solid precipitate, which is conveniently isolated.

Obtained amorphous rosuvastatin calcium of said process is chromatographically pure (over 99.5% area, mainly over 99.8% area as measured by HPLC), but may contain various amounts of residual cations, in the case of sodium hydroxide used in said hydrolysis residual amounts of sodium cation. In order to make a conversion process more repeatable in removing most of sodium cation, special care for stirring should be performed. So the precipitation of rosuvastatin calcium salt from the reaction mixture may be executed by stirring said reaction mixture with ultraturrax (Ultra-Turrax® is brand name of IKA Werke GmbH & Co., Staufen, Germany) for dispersion making device with high speed rotation unit) in operation speed from 6000 rpm to 30000 rpm, preferably from 15000 rpm to 25000 rpm, most preferably 16000 rpm to 20000 rpm. The obtained rosuvastatin calcium may also be redigested in fresh water and executing Ultraturax® stirring at the same conditions. In such preferred case content of sodium cation falls in desired rosuvastatin calcium below 0.1% by weight.

Washing of cationic impurities from the desired rosuvastatin calcium product may be carried out not only in water but also in appropriate solvent/water mixture, preferably tetrahydrofuran/water mixture.

Figure 3:
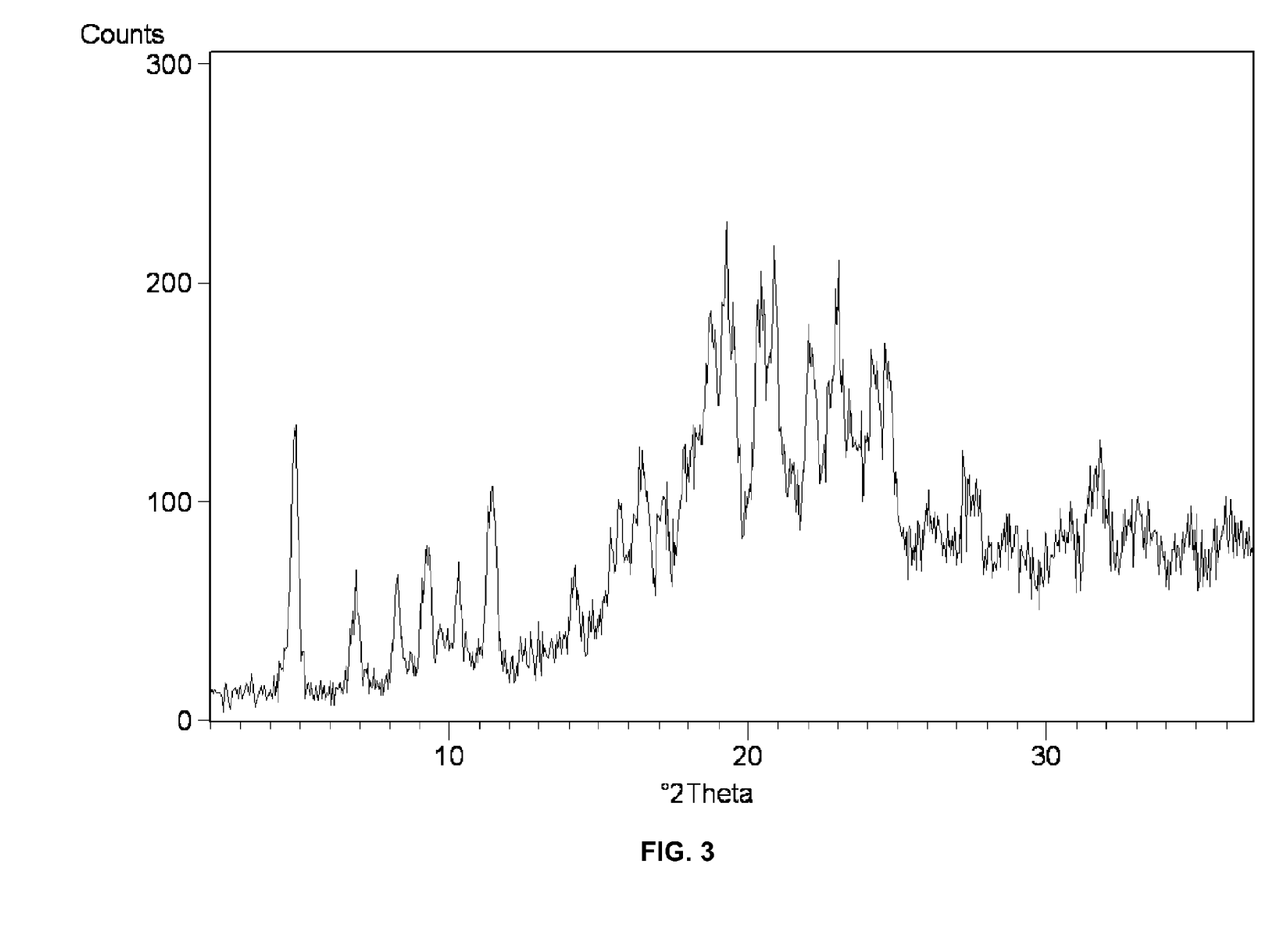
FIG. 3 is an X-ray diffractogram of a crystalline form of rosuvastatin calcium monohydrate salt.

Applying the treatment of rosuvastatin calcium with the mixture of acetone and water a monohydrate of rosuvastatin calcium salt may be prepared. Obtained crystal form of said product is identical to rosuvastatin calcium monohydrate from the prior art as proved by X-ray diffraction pattern (XRD) analysis (see FIG. 3). Rosuvastatin calcium monohydrate may be prepared by retreating any form of rosuvastatin calcium in the mixture of acetone and water or prepared by converting other rosuvastatin salts or rosuvastatin acid with calcium source in the mixture of acetone and water.

In the second aspect of the invention of using aprotic solvents and a base in hydrolysis of starting $C_1$ to $C_5$ rosuvastatin esters but in the absence of water the aprotic solvents are evaporated under the reduced pressure at temperatures from 10° C. to 50° C. The obtained salt of rosuvastatin with the base used for hydrolysis may be isolated. The preferred solvent used for said anhydrous cleavage of starting $C_1$ to $C_5$ rosuvastatin esters are amides, preferably N,N-dimethylacetamide (DMA), optionally in a combination with another solvent selected from ethers, e.g. diethyl ether. Thus the starting $C_1$ to $C_5$ ester of rosuvastatin is hydrolyzed with a base in pure DMA or in a mixture of DMA and ether in the ratio of 1:1 to 3:1 by volume. Hydrolysis may be performed at temperatures from 0° C. to 30° C. and is accomplished in 30 to 90 minutes. Precipitation of the desired rosuvastatin salt may be achieved with additional amounts of ethers, such as diethyl ether ($Et_2O$), tert-butyl methyl ether ($^tBuMeO$), diisopropyl ether ($^iPr_2O$). In such case after removing of solvents the resulted rosuvastatin salt, preferably rosuvastatin sodium salt is washed and isolated as easy filtrable solid. The term "reduced pressure" generally refers to a pressure of about 10 mbar to about 50 mbar.

Thereafter rosuvastatin sodium salt is dissolved in water and then a source of calcium ions is added. Before adding a source of calcium the aqueous solution of rosuvastatin salt of a base may be optionally washed with a water immiscible organic solvent followed by removing of said solvent. For instance calcium halogenide, preferably calcium chloride, another calcium source, for example calcium nitrate or calcium hydroxide, calcium salt of $C_1$-$C_{20}$ alkanoic acid, preferably calcium palmitate, calcium 2-ethylhexanoate, calcium pivalate or calcium acetate may be used in said conversion. Addition of $Ca(OAc)_2 \times H_2O$ may be performed at temperatures from 0° C. to 40° C.; $Ca(OAc)_2 \times H_2O$ may be added in one portion or dropwise in 5 to 60 minutes. After the addition of $Ca(OAc)_2 \times H_2O$ suspension may be stirred at temperatures between 0° C. to 40° C. from 30 minutes to 2 hours. The obtained amorphous rosuvastatin calcium is formed as a solid precipitate, which is conveniently isolated. Also in this aspect residual amounts of sodium cation containing in rosuvastatin calcium may be reduced with special care on stirring and redigesting, as described above.

Rosuvastatin calcium salt isolated according to any of previously described procedures is in amorphous form. The final product rosuvastatin calcium may be conveniently isolated also as a solvate, preferably as rosuvastatin calcium monohydrate, which may be isolated from the mixture of acetone and water added to rosuvastatin calcium, preferably from the mixture of acetone and water in the ratio of 2:1 by volume, what is more simple procedure as already known long drawn procedure from the prior art.

Described procedure provides a desired rosuvastatin calcium of high purity where according to the first aspect of the invention the purity of so produced rosuvastatin calcium exceeds 99.8% area, preferably 99.9% area, while according to the second aspect the produced rosuvastatin calcium exceeds 99.5% area, preferably 99.7% area as measured by HPLC.

In the third aspect of the invention the use of aprotic solvents in the hydrolysis of starting $C_1$ to $C_5$ rosuvastatin esters enables an isolation of pure solid rosuvastatin acid. Performing hydrolytic conditions previously described as aprotic solvent—water mixture and a base and after removing most of organic solvents from the resulted aqueous solution of rosuvastatin salt is acidified with an inorganic acid, preferably hydrochloric acid, and rosuvastatin free acid is extracted into a water immiscible or partially miscible organic solvents, for example ethers, esters, chlorinated hydrocarbons, preferably $C_1$-$C_4$ acetate esters, most preferably ethyl acetate (AcOEt).

Isolation of rosuvastatin solid free acid or preparation of pure rosuvastatin free acid solution according to the invention makes possible a preparation of various new amine salts of rosuvastatin and various anhydrous rosuvastatin salts. In hereinafter presented examples tert-octylammonium (2,4,4-trimethyl-2-pentylammonium) rosuvastatin salt and anhydrous rosuvastatin calcium salt may be prepared. The preparation of rosuvastatin amine salt may be performed in acetonitrile (MeCN) as a solvent by adding tert-octylamine (2,4,4-trimethyl-2-pentylamine) to the rosuvastatin free acid solution, following filtering off the rosuvastatin tert-amine salt precipitate after completing of the reaction.

The preparation of anhydrous amorphous rosuvastatin calcium salt may also be performed in iso-butyl acetate solvent by adding calcium 2-ethylhexanoate to the rosuvastatin free acid solution, following filtering off the precipitate of amorphous rosuvastatin calcium. Substantially anhydrous rosuvastatin calcium may be used in special pharmaceutical formulations of the present invention in which the absence of water is desired. The term "substantially anhydrous" means that the content of water in anhydrous rosuvastatin calcium is less than 0.1% by weight.

The various aspects of the invention are presented in the following scheme 2 and described in detail in following examples:

(M⁺ denotes alkali metal cation, e.g. sodium cation)

Analytical Method

Chromatographic purity is determined by HPLC method by the following method: Equipment: Waters Alliance 2695 separations module, detector PDA 2996, software Empower 5.0; column: Xterra RP 18, 3 µm, 150×4.6 mm; mobile phase: A: Buffer 10 mM $KH_2PO_4$, pH=2.5; B: acetonitrile; temperature: 45° C.; flow rate: 1.2 ml/min; wavelength: 224 and 242 nm; injection volume: 20 µl; gradient table:

| t | % A | % B |
|---|-----|-----|
| 0 | 60 | 40 |
| 15 | 60 | 40 |
| 25 | 50 | 50 |
| 25 | 30 | 70 |
| 40 | 30 | 70 |
| 41 | 60 | 0 |

Powder X-ray diffraction spectra of the sample is recorded on Siemens D-5000, CuKα radiation, range from 20 to 37° 2θ, step 0.04°2θ, integration time 1 sec, slit V20 in 0.6.

EXAMPLE 1

Preparation of Rosuvastatin Calcium Salt via Rosuvastatin Sodium Salt Solution

Rosuvastatin tert-butyl ester (60.0 g, 111.6 mmol) is dissolved in 500 mL of a 4:1 mixture of THF/water. The clear solution is warmed to 30° C. and 8.0 M NaOH (15 mL, 120.0 mmol) is added portionwise. The reaction mixture is stirred at 30° C. for 2 hours giving a clear yellow solution. Then THF is removed completely under the reduced pressure (20 mbar) at 40° C. The remaining aqueous solution is diluted with water to 500 mL and washed with AcOEt (2×200 mL). After separation from the organic layer aqueous phase is distilled under the reduced pressure (20 mbar) at 40° C. to completely remove the dissolved AcOEt. The remaining clear solution of sodium rosuvastatinate (440 mL) is diluted with water (60 mL) to 500 mL and warmed to 40° C. To a vigorously stirring solution of sodium rosuvastatinate is added dropwise $Ca(OAc)_2 \times H_2O$ (14.8 g, 84.0 mmol in 60 mL of water) over 5 minutes at 40° C. to precipitate rosuvastatin calcium. After the complete addition the suspension is stirred further for 30 minutes at 40° C. The white precipitate is filtered off. Then a wet white solid is suspended in water (200 mL) and vigorously stirred for 1 hour at 20° C. The undissolved precipitate is collected by filtration, washed with water (200 mL) and dried in vacuum at 40° C. to give 48.5 g (86.8%) of rosuvastatin calcium salt as white powder (HPLC: 99.87%).

EXAMPLE 2

Rosuvastatin tert-butyl ester (60.0 g, 111.6 mmol) is dissolved in 120 mL of tetrahydrofuran (THF) and 300 ml of water treated 8.0 M NaOH (21 mL) is added portionwise. The reaction mixture is stirred at 50° C. for 2 hours. Reaction mixture is allowed to cool to room temperature and washed with 2×540 ml of methylcyclohexane.

Aqueous phase is evaporated at 60° C. under reduced pressure to 220 ml of total volume to eliminate organic solvents. The residue obtained is rediluted with degassed demi-water to 440 ml of total volume. To the resulting solution 1.0 g of charcoal is added and the suspension is stirred half an hour. Charcoal is filtered off. One half of the volume of the filtrate (220 ml of total 440 ml) 25.5 ml aqueous solution of calcium chloride (prepared from 10.5 ml 4M calcium chloride and 15 ml demi-water) is added during stirring on ice-bath. The suspension formed is treated vigorously with ultraturrax at cca 18000 rpm for 3 minutes. The precipitate is filtered off, suspended anew in 100 ml demi water and treated again with Ultraturax® at 18000 rpm for 3 minutes on ice-bath. The product is separated by filtration, washed with 30 ml ice-cold degassed demi-water, collected from the filter and dried 12 hours at 50° C. in vacuum desiccator.

Yield: 25.05 g of amorphous rosuvastatin calcium (99.75% area, HPLC, 0.085% Na)

The second aliquot of 220 ml of filtrate is treated on the same way except mechanical stirring instead of ultraturax mixing is performed. Yield 25.11 g (99.72% area, HPLC, 1.55% Na)

EXAMPLE 3

Rosuvastatin tert-butyl ester (10.0 g) is dissolved in 20 mL of tetrahydrofuran and 50 ml of water treated 8.0 M NaOH (3.51 mL) is added portionwise. The reaction mixture is stirred at 50° C. for 1 hours. One third (26 ml of the total 78 ml) of the resulting solution is washed with 35 ml methylcyclohexane. Methylcyclohexane phase is extracted with 3 ml demi water. Combined aqueous phases are washed with 20 ml iso-propyl acetate. Aqueous phase is then concentrated by evaporation under reduced pressure at 50° C. to 15-20 ml of total volume. It is cooled on ice-bath and gradually 1.1 ml aqueous solution of 4M calcium chloride is added within a minute during stirring. It is stirred additional 30 minutes on ice-bath and the precipitated product is separated by filtration. The precipitate is washed with 4.0 ml demi water, collected from the filter and dried at room temperature 12 hours in vacuum desiccator.

Yield: 2.22 g of amorphous rosuvastatin calcium.

Two further aliquots are washed with 20 ml ethyl acetate or 20 ml tert-butyl methyl ether respectively with similar yield and quality.

EXAMPLE 4

Preparation of Rosuvastatin Sodium Salt

Rosuvastatin tert-butyl ester (3.0 g, 5.6 mmol) is dissolved in 25 mL of a 4:1 mixture of THF/water. The clear solution is warmed to 30° C. and 8.0 M NaOH (0.75 mL, 6.0 mmol) was added portionwise. The reaction mixture is stirred at 30° C. for 2 hours giving a clear yellow solution. Then THF is removed completely under the reduced pressure (20 mbar) at 40° C. The remaining aqueous solution is diluted with water to 25 mL and washed with AcOEt (2×10 mL). After separation from the organic layer aqueous phase is distilled under the reduced pressure (20 mbar) at 40° C. to completely remove the dissolved AcOEt. The remaining clear solution of sodium rosuvastatinate is diluted with water to 25 mL and liophylized to afford 2.81 g (100%) of rosuvastatin sodium salt as white powder.

EXAMPLE 5

Rosuvastatin tert-butyl ester (3.0 g, 5.6 mmol) is dissolved in N,N-dimethylacetamide (4 mL) at ambient temperature giving a clear yellow solution. Then NaOH 8.0 M (0.75 mL, 6.0 mmol) is added dropwise to a stirred solution at ambient temperature. The reaction mixture is stirred at ambient temperature for 30 minutes giving a clear yellow solution. Then $Et_2O$ (50 mL) is added portionwise to the vigorously stirred reaction mixture which becomes immediately turbid and light yellow oil separated from the mixture. After 20 minutes of vigorous stirring oil solidified and fine white precipitate is formed. The suspension is stirred at ambient temperature for 2.5 hours. The white precipitate (sodium rosuvastatinate) is filtered off and washed with $Et_2O$ (2×20 mL).

EXAMPLE 6

Preparation of Rosuvastatin Calcium Salt from Isolated Rosuvastatin Sodium Salt

Rosuvastatin sodium as white solid from Example 5 is dissolved in water (30 mL) and solution is filtered to give clear colourless solution. The pH of solution is adjusted to 7 by addition of 1.0 M HCl (0.5 mL). To a vigorously stirring solution of sodium rosuvastatinate is added dropwise $Ca(OAc)_2 \times H_2O$ (0.74 g, 4.2 mmol in 3 mL of water) over 1 minute at ambient temperature to precipitate rosuvastatin calcium. After the complete addition the suspension is stirred further for 45 minutes at ambient temperature. The white precipitate is filtered off, washed with water (2×10 mL) and dried in vacuum at 40° C. to give 2.43 g (87.0%) of rosuvastatin calcium salt as white powder (HPLC: 99.72%).

EXAMPLE 7

Preparation of Crystalline Rosuvastatin Calcium Monohydrate Salt

To a rosuvastatin calcium salt (2.0 g, 2.0 mmol) is added 10 mL of a 2:1 mixture of acetone/water. The mixture is stirred at ambient temperature for 30 minutes to give a white turbid solution. Then additional 1 mL of a 2:1 mixture of acetone/water is added into the mixture. After 10 minutes of stirring at ambient temperature white solid precipitates abundantly from the mixture. The precipitate is collected by filtration. After drying in vacuum at 40° C. 1.67 g (82.0%) of crystalline rosuvastatin calcium monohydrate salt is obtained. Crystalline form is confirmed by comparing diffractogram (FIG. 3) with reference picture from the prior art.

EXAMPLE 8

Preparation of Solid Rosuvastatin Free Acid

Rosuvastatin tert-butyl ester (27.0 g, 50.2 mmol) is dissolved in 225 mL of a 4:1 mixture of THF/water. The clear solution is warmed to 30° C. and 8.0 M NaOH (6.75 mL, 54.0 mmol) is added portionwise. The reaction mixture is stirred at 30° C. for 2 hours giving a clear yellow solution. Then THF is removed completely under the reduced pressure (20 mbar) at 40° C. The remaining aqueous solution is diluted with water to 225 mL and washed with AcOEt (3×90 mL). To a vigorously stirring solution of sodium rosuvastatinate is added dropwise HCl 37% (4.2 mL, 50.2 mmol) at ambient temperature. The obtained white emulsion of a free acid is extracted with AcOEt (150 mL). After separation from the organic layer aqueous phase is additionaly extracted with AcOEt (2×50 mL). Organic layers are combined and washed with water (3×30 mL). Then AcOEt is removed under reduced pressure (20 mbar) at 40° C. The residue is dissolved in a minimal amount of acetonitrile (MeCN) and the solvent is rapidly evaporated under reduced pressure (20 mbar) at 40° C. to give 25.48 g of the solid residue of free rosuvastatin acid.

EXAMPLE 9

Preparation of Crystalline Tert-Octylammonium Salt of Rosuvastatin

Solid free rosuvastatin acid is then dissolved in acetonitrile (MeCN) (100 mL) to give a clear solution. To a vigorously stirring solution of a rosuvastatin free acid is added dropwise tert-octylamine (6.83 g, 50.2 mmol) over 1 minute at ambient temperature. In less then 10 minutes white solid precipitates abundantly from the solution, which cause solidification of the mixture. This solid is then treated with 75 mL of a 1:2 mixture of hexane/MeCN to give a dense suspension. The white precipitate is filtered and dried in vacuum at 40° C. to give 27.6 g of a white powder. This powder is suspended in hexane (100 mL) and vigorously stirred for 1 hour at ambient temperature. The undissolved precipitate is collected by filtration, washed with hexane (50 mL) and dried in vacuum at 40° C. to give 27.4 g (89.4%) of rosuvastatin tert-octylammonium salt as white crystalline powder.

EXAMPLE 10

20.0 g of rosuvastatin tert-butyl ester is dissolved in the mixture of 40 ml of tetrahydrofuran and 100 ml of water, then 7.0 ml 8M NaOH is added and stirred at 40° C. for 1 hour. The resulting solution is washed with 200 ml methylcyclohexane. Methylcyclohexane phase is extracted with 5 ml demi water. Aqueous phases are combined getting 140 ml of total volume of rosuvastatin sodium salt solution.

To this solution 180 ml iso-butyl acetate and 5.4 ml 85% ortho-phosphoric acid in 21 ml of demi water is added, wherein released free rosuvastatinic acid is extracted in the organic phase and the layers formed are separated. To the organic phase 3.0 g charcoal and 30 g anhydrous magnesium sulfate are added and the resulting suspension is stirred 45 minutes. The following filtration yielded 240 ml of filtrate.

To the filtrate the solution of 84 ml of 0.4 M calcium 2-ethylhexanoate in iso-butyl acetate is added. Then, to the reaction mixture 240 ml of n-heptane is gradually added during stirring on the ice-bath. The solid precipitate is filtered off and washed with 120 ml iso-butyl acetate/n-heptane mixture (1:1).

Yield: 19.7 g of amorphous rosuvastatin calcium is collected after drying.

The invention claimed is:
1. A process for producing pure amorphous rosuvastatin calcium which comprises:
  a) hydrolysing a $C_1$ to $C_5$ alkyl ester of rosuvastatin with a base in the presence of an aprotic solvent or with a base in the presence of a mixture of an aprotic solvent and water to obtain an aqueous solution of rosuvastatin salt;
  b) converting the thus obtained rosuvastatin salt in the solution with a source of calcium to obtain amorphous rosuvastatin calcium; and
  c) isolating the amorphous rosuvastatin calcium from the solution
  wherein the aprotic solvent comprises tetrahydrofuran or N,N-dimethylacetamide.
2. The process according to claim 1, wherein the $C_1$ to $C_5$ alkyl ester of rosuvastatin comprises tert-butyl rosuvastatin.
3. The process according to claim 1, wherein the aprotic solvent comprises tetrahydrofuran.
4. The process according to claim 3, wherein the ratio of tetrahydrofuran and water ranges from about 5:1 to about 1:5 by volume.
5. The process according claim 3, wherein the ratio of tetrahydrofuran and water ranges from about 4:1 to about 1:3 by volume.
6. The process according to claim 1, wherein the base comprises sodium hydroxide.
7. The process according to claim 1, wherein the source of calcium is selected from the group consisting of calcium chloride, calcium nitrate, calcium hydroxide and a calcium salt of $C_1$-$C_{20}$ alkanoic acid.
8. The process according to claim 7, wherein the calcium salt of $C_1$-$C_{20}$ alkanoic acid is selected from the group consisting of calcium palmitate, calcium pivalate and calcium acetate.
9. The process according to claim 1, wherein the rosuvastatin calcium is isolated from the solution in a solid form.
10. A process for producing amorphous rosuvastatin calcium, which comprises the steps of:
  a) hydrolyzing a $C_1$ to $C_5$ alkyl ester of rosuvastatin by contacting the same with a mixture including a base in an aprotic solvent;
  b) removing the aprotic solvent from the mixture to obtain a residue;
  c) combining the residue with water to obtain an aqueous solution of rosuvastatin salt of the base;
  d) optionally washing the obtained aqueous solution with a water immiscible organic solvent;
  e) optionally removing organic solvent from the solution;
  f) adding a source of calcium to the solution to precipitate a rosuvastatin calcium salt therefrom; and
  g) isolating the amorphous rosuvastatin calcium salt precipitate from the solution
  wherein the aprotic solvent comprises tetrahydrofuran or N,N-dimethylacetamide.
11. The process according to claim 10, wherein the aprotic solvent comprises N,N-dimethylacetamide, optionally in combination with an ether.
12. The process according to claim 11, wherein the ether comprises diethyl ether and the ratio of N,N-dimethylacetamide to diethyl ether ranges from about 1:1 to about 3:1 by volume.
13. The process for producing amorphous rosuvastatin calcium according to claim 10, wherein the mixture prepared in step a) is treated by ultraturrax.
14. A process for producing rosuvastatin free acid, which comprises the steps of:
  a) hydrolysing a $C_1$ to $C_5$ alkyl ester of rosuvastatin by contacting the same with an aqueous mixture including a base in an organic aprotic solvent;
  b) substantially removing any excess organic aprotic solvent from the mixture, thereby leaving an aqueous solution containing dissolved rosuvastatin salt therein;
  c) optionally diluting the aqueous solution with additional water;
  d) optionally washing the obtained aqueous solution containing the rosuvastatin salt of the base with a water immiscible organic solvent;

e) acidifying the aqueous solution containing the rosuvastatin salt of the base to form rosuvastatin acid therein;

f) extracting the rosuvastatin acid with a water immiscible organic solvent; and g) removing the water immiscible organic solvent from the rosuvastatin acid extract to obtain isolated rosuvastatin free acid wherein the aprotic solvent comprises tetrahydrofuran or N,N-dimethylacetamide.

15. The process according to claim 14, wherein the $C_1$ to $C_5$ alkyl ester of rosuvastatin comprises methyl rosuvastatin.

16. The process according to claim 14, wherein the $C_1$ to $C_5$ alkyl ester of rosuvastatin comprises tert-butyl rosuvastatin.

17. The process according to claim 14, wherein the alkyl group of the $C_1$ to $C_5$ alkyl ester of rosuvastatin denotes a methyl, ethyl, n-propyl, iso-propyl, n-butyl, iso-butyl, tert-butyl, amyl, or tent-amyl group.

18. The process according to claim 10, wherein the water immiscible solvent comprises ethyl acetate.

19. The process according to step e) of claim 14, wherein hydrochloric acid is used for acidifying the aqueous solution.

20. A process for producing a rosuvastatin salt, wherein rosuvastatin free acid is contacted with a cation source in an organic solvent.

21. The process for producing a rosuvastatin salt according to claim 20, wherein isolated rosuvastatin free acid is contacted with a calcium source in the organic solvent.

22. The process for producing rosuvastatin calcium according to claim 20, wherein the organic solvent is selected from the group consisting of $C_2$ to $C_4$ alkyl acetate esters.

23. The process for producing rosuvastatin calcium according to claim 20, wherein the rosuvastatin free acid comprises a water content of less than 0.1% by weight.

24. The process for preparing rosuvastatin calcium according to claim 20, wherein the cation source is a source of calcium ions comprising calcium 2-ethylhexanoate.

25. The process for preparing rosuvastatin salt according to claim 20, wherein isolated rosuvastatin free acid is contacted with a source of calcium ions in a mixture comprising acetone and water to form rosuvastatin calcium monohydrate in the mixture.

26. The process for preparing rosuvastatin salt according to claim 25, wherein the salt comprises amorphous rosuvastatin calcium.

27. Amorphous rosuvastatin calcium in solid state, prepared according to claim 1, having a purity of more than 99.8% as measured by area percentage using HPLC.

28. Amorphous rosuvastatin calcium in solid state, prepared according to claim 1, having a purity of more than 99.9% as measured by area percentage using HPLC.

29. Substantially anhydrous rosuvastatin calcium comprising a water content of less than 0.1% by weight.

30. A pharmaceutical formulation for administration to a mammal in need of a reduction in blood cholesterol level comprising amorphous rosuvastatin calcium prepared according to claim 1.

31. A method of treating a mammal in need of a reduction in blood cholesterol level comprising the step of administering the pharmaceutical formulation of claim 30 to the mammal in need thereof.

32. The process for producing amorphous rosuvastatin calcium according to claim 1, wherein the mixture prepared in step a) is treated by ultraturrax.

33. The process according to claim 1, wherein the alkyl group of the $C_1$ to $C_5$ alkyl ester of rosuvastatin denotes a methyl, ethyl, n-propyl, iso-propyl, -butyl, iso-butyl, tert-butyl, amyl, or tert-amyl group.

34. The process according to claim 10, wherein the alkyl group of the $C_1$ to $C_5$ alkyl ester of rosuvastatin denotes a methyl, ethyl, n-propyl, iso-propyl, -butyl, iso-butyl, tert-butyl, amyl, or tert-amyl group.

35. The process according to claim 10 wherein the water immiscible organic solvent comprises ethyl acetate.

36. Amorphous rosuvastatin calcium prepared according to claim 13, comprising a sodium cation content below 0.1% by weight.

37. Amorphous rosuvastatin calcium prepared according to claim 32, comprising a sodium cation content below 0.1% by weight.

38. Amorphous rosuvastatin calcium comprising a sodium cation content below 0.1% by weight.

* * * * *